US00PP34702P3

(12) United States Plant Patent
Olesen et al.

(10) Patent No.: US PP34,702 P3
(45) Date of Patent: Nov. 1, 2022

(54) ***CLEMATIS* PLANT NAMED 'EVIPO109'**

(50) Latin Name: *Clematis viticella*
Varietal Denomination: 'Evipo109'

(71) Applicants: Mogens Nyegaard Olesen, Fredensborg (DK); Raymond J Evison, Guernsey (GB)

(72) Inventors: Mogens Nyegaard Olesen, Fredensborg (DK); Raymond J Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,636

(22) Filed: Sep. 7, 2021

(65) Prior Publication Data

US 2022/0095519 P1 Mar. 24, 2022

(30) Foreign Application Priority Data

Sep. 21, 2020 (QZ) ..... 2020/2281

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

(56) References Cited

PUBLICATIONS

CPVO Register; https://online.plantvarieties.eu/publicSearch?denomination=evipo109 Retrieved from the Internet Oct. 26, 2021, citation for 'Evipo109'.*

* cited by examiner

*Primary Examiner* — Susan McCormick Ewoldt

(57) ABSTRACT

A new *Clematis* plant with a compact growth habit, profuse, violet blue flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

3 Drawing Sheets

Botanical classification: Genus: *Clematis*. Species: *viticella*.

Variety denomination: 'Evipo109'.

This application claims priority to Plant Breeder's Rights Application Number 2020/2281, which was filed at the Community Plant Variety Rights Office in the European Union on Sep. 21, 2020, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo109' originated as a single seedling from the stated cross.

The new *Clematis* plant may be distinguished from its female seed parent and male pollen parent by the following characteristics. The female seed parent grows to a height of 75 cm while the new variety grows to 38 cm in one season. The male seed parent has light violet tepals while the new variety has violet-blue tepals.

The objective of the hybridization of this *Clematis* plant was to create a new and distinct variety for nursery culture with unique qualities such as:

1. Uniform and abundant violet-blue flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo109' was selected by Mogens N. Olesen and Raymond J. Evison in their *Clematis* development program in Vale, Guernsey located in the Channel Islands, United Kingdom in 2008. Asexual reproduction of 'Evipo109' by means of vegetative cuttings and traditional layering was first performed by Mogens N. Olesen and Raymond J. Evison in the nursery in Guernsey during the summer of 2008. This initial and subsequent asexual propagations have demonstrated that the characteristics of 'Evipo109' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo109'.

Specifically illustrated in FIG. 1 of the drawings are open flowers, tepals detached showing reproductive flower parts.

DETAILED DESCRIPTION OF THE VARIETY

Figure 1:
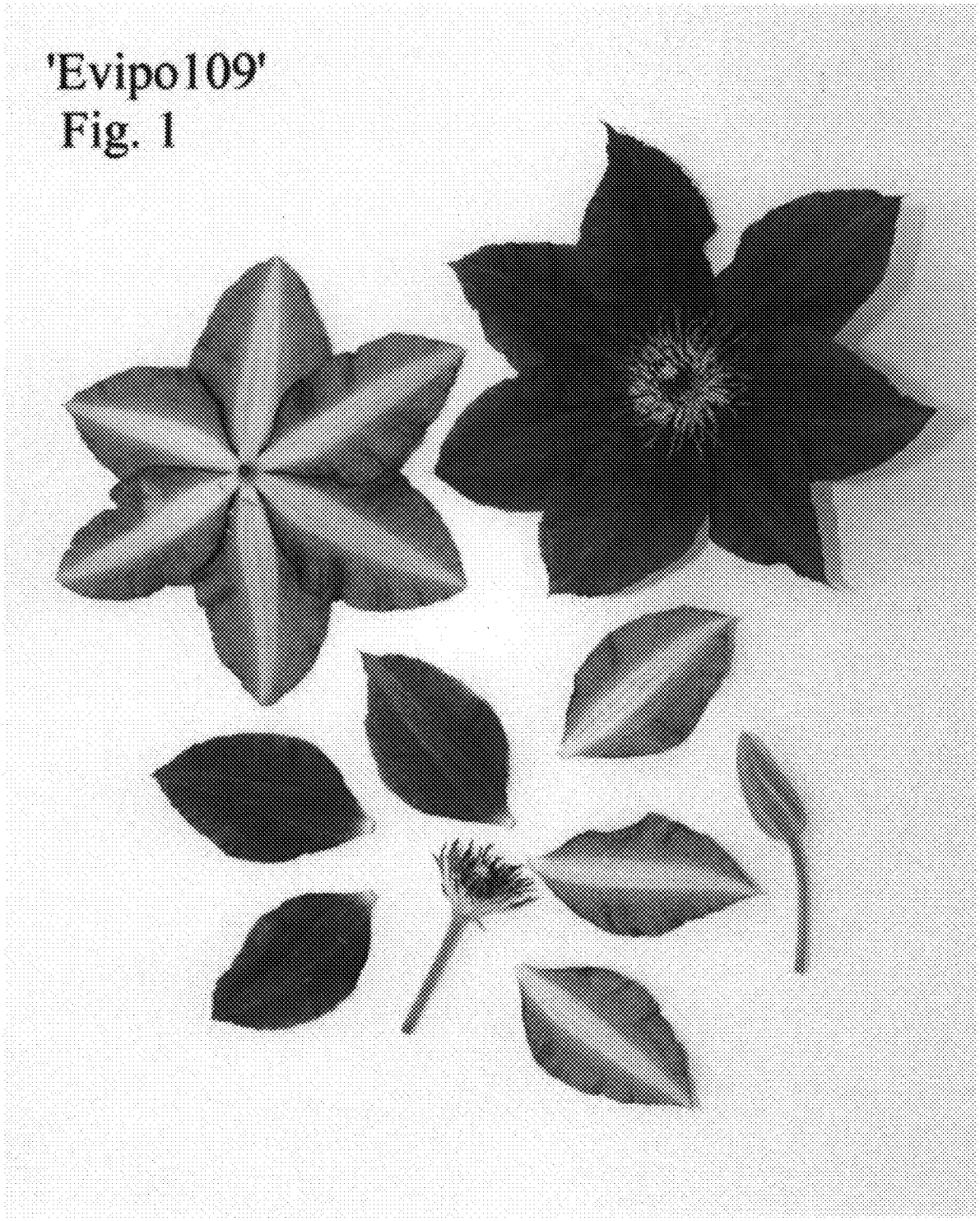
Figure 2:
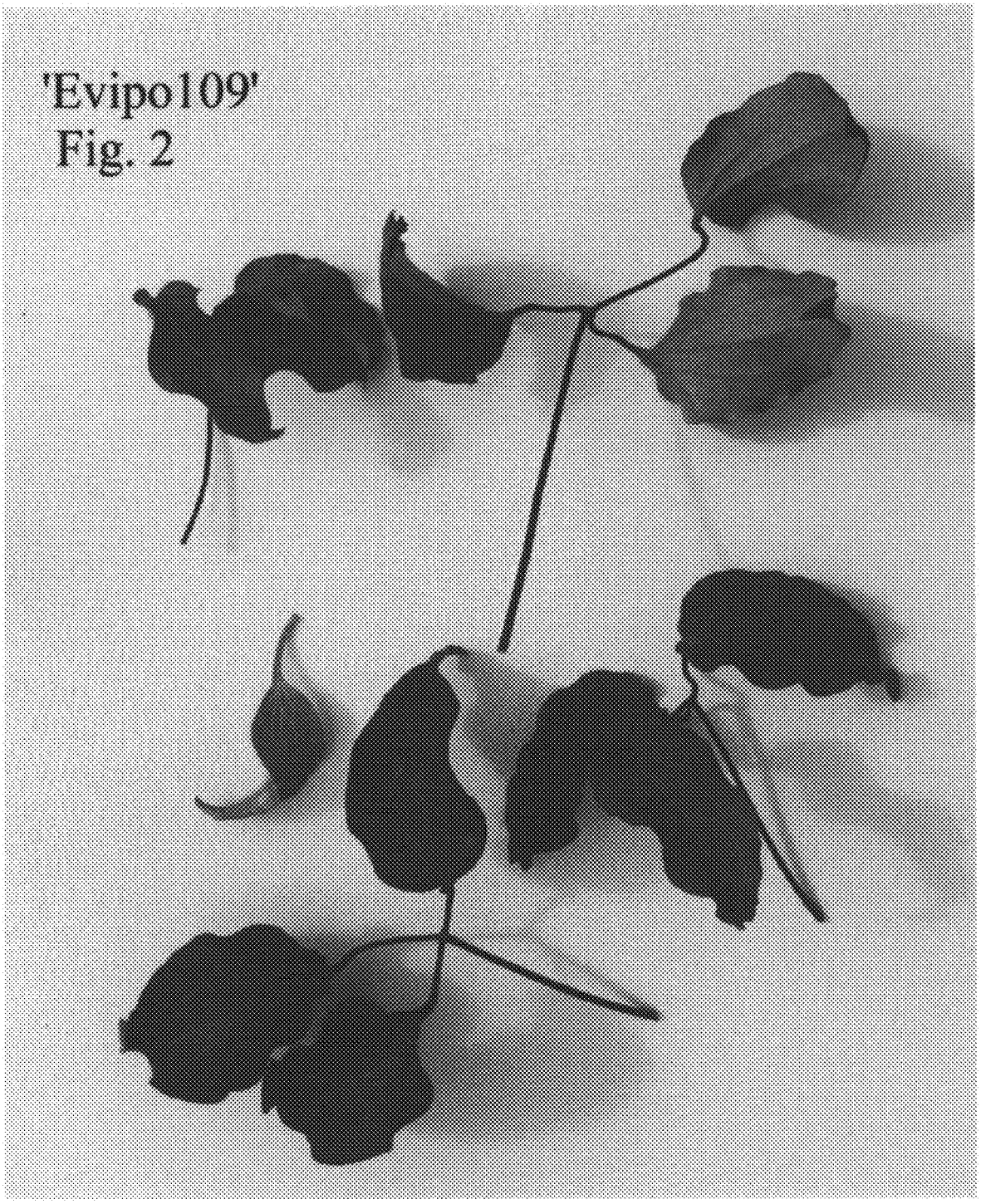
FIG. 2 shows leaves.
Figure 3:
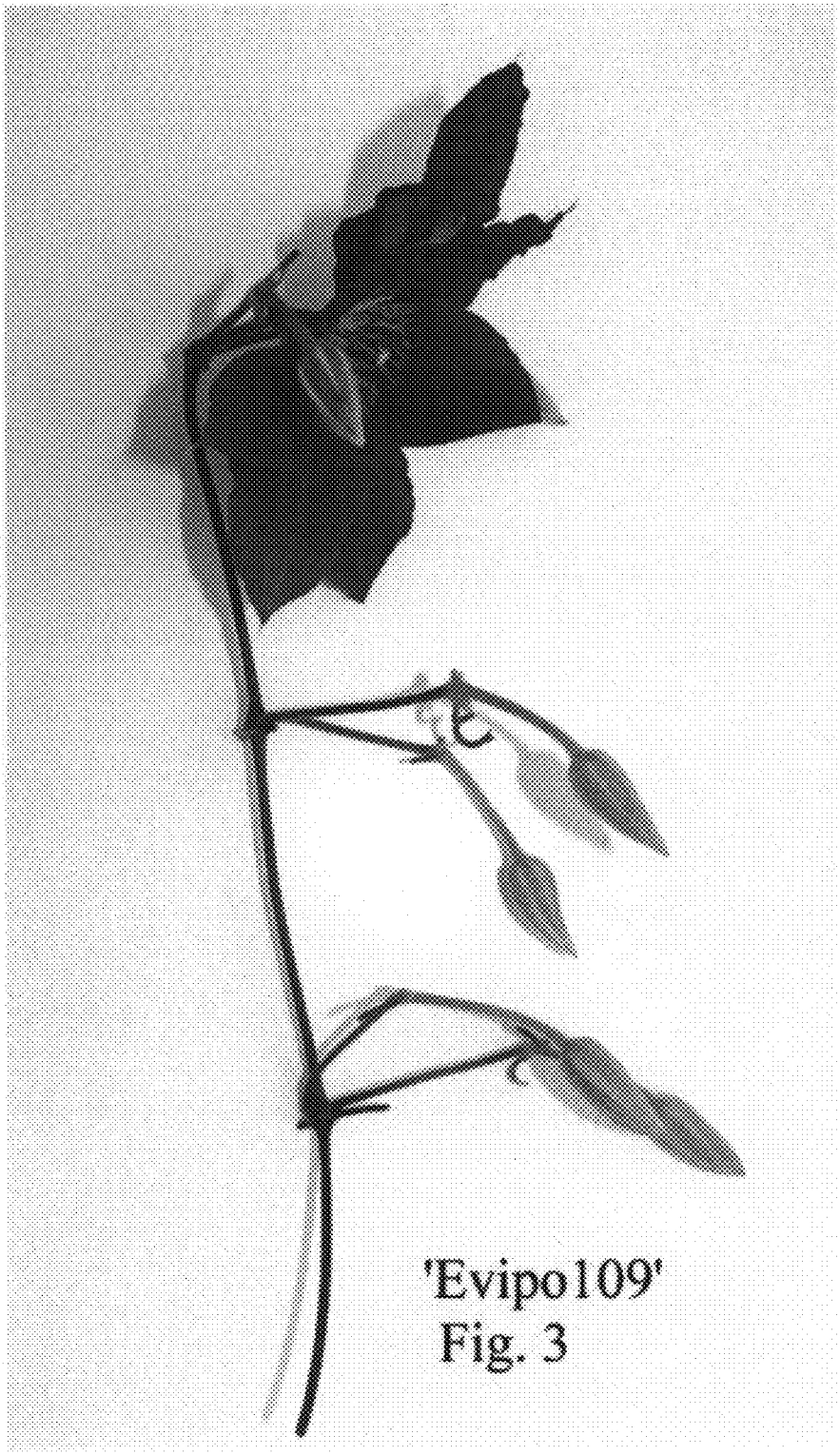
FIG. 3 shows a flowering branch with open flower and flower buds attached. Illustrated plants are 2 years of age.

The following is a detailed description of 'Evipo109', as observed in its growth outdoor throughout the flowering period in Odense Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo047' described and illustrated in U.S. Plant Pat. No. 28,371 are compared to 'Evipo109' in Chart 1.

CHART 1

| | 'Evipo109' | 'Evipo047' |
|---|---|---|
| Flower diameter | 130 mm | 80 mm |
| Tepal upper surface | Violet-Blue Group N89B with intonations of Violet Group 86A | Violet Group N88C with intonations of Purple-Violet Group N81B |
| Tepal count | Normally 6 to 7 | 13 to 15 |

Flower and flower bud:

Blooming habit: Continuous. The natural flowering period is generally from April to September.

Flower bud:

*Size*.—Normally 25 mm in length. Bud diameter is 10 mm.

*Bud form*.—Long campanulate, broad based.

*Bud color*.—Yellow-Green Group 145B.

*Texture*.—Highly Pubescent.

Pedicel:

*Surface texture*.—Pubescent.

*Length*.—On average 21 mm in length with 2.5 to 3 mm diameter.

*Color*.—Yellow-Green Group 145B.

*Strength*.—Moderately strong.

Receptacle:

*Surface texture*.—Lightly pubescent.

*Shape*.—Broad funnel.

*Size*.—1.5 mm (h)×4 mm (w).

*Color*.—Yellow-Green Group 145B

Flower arrangement:

*Location on vine*.—New growth only.

*Borne*.—In multiples of 2 at each axillary bud.

Flower bloom:

*Size*.—Average 130 mm in diameter and 30 mm in depth.

*Profile*.—Almost flat.

*Fragrance*.—Light pollen scent.

*Lasting quality*.—Flowers normally remain up to 15 days on the plant.

Tepals:

*Tepal color*.—Upon opening, the upper surface is Violet-Blue Group N89B with intonations of Violet Group 86A. Apex is White Group 155A. The lower surface Violet Group N88B with a marginal thin layer of Violet Group 86B. There is a central bar the color of White Group N155B.

*Quantity*.—Normally 6 to 7 tepals.

*Size*.—68 mm in length by 40 mm wide.

*Shape*.—Individual tepal shape is elliptical. The tepal apex is acuminate. The tepal base is attenuate.

*Apex recurvature*.—None.

*Tepal cross section*.—Flat.

*Margins*.—Entire. Strong undulations.

*Persistence*.—Tepals drop off cleanly.

Reproductive organs:

*Pollen*.—None observed.

*Anthers*.—Size: 5 mm in length. Color: Greyed-Purple Group N186C and D. Quantity: On average, 35.

*Filaments*.—Color: White Group N155B. Length: 7 mm.

*Pistils*.—Quantity: On average, 20.

*Stigmas*.—Slightly superior in location relative to the length of the filaments and the height of the anthers.

*Styles*.—Color: White Group 155A. Length: 12 mm.

Seed head characteristics: Seed not observed to date.

Plant

Plant form: Mounding, or prostrate.

Plant growth: Moderately vigorous.

Size: Seasons growth attains 38 cm in height. Average spread is 30 cm.

Stems:

*Color*.—Juvenile stems are Yellow-Green Group 145B. Mature stems are Greyed-Purple Group 183A.

*Internodes*.—On average, 8 cm between nodes.

*Length*.—Normally 10 cm from the base of the plant to the flowering portion of the stem.

*Diameter*.—About 3 mm.

*Texture*.—Mature stems are smooth and lightly pubescent.

Plant foliage:

*Leaf characteristics*.—Deciduous.

*Arrangement*.—Trifoliate.

*Leaf size*.—Compound leaves are about 145 mm (l)× 120 mm (w). Leaflets are about 45 to 60 mm (l)×32 mm (w).

*Abundance*.—On average leaves per 10 cm of stem.

*Leaf color*.—Juvenile upper Yellow-Green Group 144A. Juvenile lower Yellow-Green Group 144A. Mature upper Yellow-Green Group 146B. Mature lower Yellow-Green Group 146C.

*Stipules*.—Absent.

*Petioles*.—Size: Normally 70 mm in length by mm diameter. Texture: Smooth. Color: Yellow-Green Group 144A.

*Petioloule*.—Size: About 10 to 25 mm in length by 2 mm diameter. Texture: Smooth. Color: Greyed-Purple Group N186C.

*Leaflet shape*.—Deltoid. The base is rounded, apex acute.

*Margin*.—Entire. Strong or weak undulations.

*Surface*.—The upper side is smooth, the lower side is smooth.

*Thickness*.—Moderate.

*Glossiness*.—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo109', substantially as described and illustrated , due to its abundant violet-blue flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo109'

'Evipo109'

'Evipo109'